United States Patent [19]
Loiez nee Hennette et al.

[11] Patent Number: 5,741,695
[45] Date of Patent: Apr. 21, 1998

[54] STRAINS OF BREAD-MAKING YEAST, A PROCESS FOR OBTAINING SAME, AND THE CORRESPONDING FRESH AND DRY NEW YEAST

[75] Inventors: Annie Loiez nee Hennette, Roland; Philippe Clement, rue de Barbieux; Didier Colavizza, Impasse Berthelof, all of France

[73] Assignee: Lesaffre et Cie, Paris, France

[21] Appl. No.: 285,768

[22] Filed: Aug. 3, 1994

Related U.S. Application Data

[63] Continuation of Ser. No. 80,131, Jun. 23, 1993, abandoned, which is a continuation of Ser. No. 872,395, Apr. 23, 1992, abandoned.

[30] Foreign Application Priority Data

Apr. 23, 1991 [FR] France .................. 91 05008

[51] Int. Cl.$^6$ .................. C12N 1/18; A23L 1/28
[52] U.S. Cl. .................. 435/255.2; 426/62
[58] Field of Search .................. 426/62; 435/172.3, 435/254.21, 254.2, 255.2

[56] References Cited

U.S. PATENT DOCUMENTS

| | | | |
|---|---|---|---|
| 4,318,929 | 3/1982 | Clement et al. | 426/62 |
| 4,318,930 | 3/1982 | Clement et al. | 426/62 |
| 4,396,632 | 8/1983 | Clement et al. | 426/62 |

FOREIGN PATENT DOCUMENTS

| | | |
|---|---|---|
| 895475 | 12/1982 | Belgium . |
| 8554 | 8/1980 | European Pat. Off. . |
| 128524 | 6/1983 | European Pat. Off. . |
| 229976 | 7/1987 | European Pat. Off. . |
| 306107 | 3/1989 | European Pat. Off. . |
| 2393062 | 12/1978 | France . |
| 1539211 | 1/1979 | United Kingdom . |
| 1590830 | 6/1981 | United Kingdom . |

OTHER PUBLICATIONS

"Isolation of *Saccharomyces cerevisiae* Mutants Constitutive for Invertase Synthesis" of Robert J. Trumbly, Journal of Bacteriology, Jun. 1986, vol. 166, p. 1123.
"The Yeasts" edited by A.H. Rose and J.S. Harrison, 1969, Academic Press—Chapter 7.
"Sporulation and Hybridization of Yeasts" (book cover page and first page of Chapt. 7).
Taussig et al. (1983) Nucleic Acids Research, vol. 11, No. 6, pp. 1943–1954.
Halvorson et al. (1958) Biochimica et Biophysica Acta, vol. 30, pp. 28–40.
Winnacker (1987) From Genes to Clones, VCH Verlagsgesellschaft mbH, Weinheim, Germany, pp. 183–188.
Nagodawithana, Tilak and Trivedi, Nayan B. (1990) Yeast Selection for Baking in Panchal, Chandra J. (Ed.) Yeast Strain Selections. NY: Marcel Dekker.
Trivedi, Nayan B., Jacobson, Gunnard K. and Tesch William (1986) Bakers's Yeast. CRC Crit. Review in Biotechnol. 4(1) 75–109.
Rothstein, Rodney J. (1983) One–Step Gene Disruption in Yeast. Methods in Enzymology 101:202–211.
World Patents Index Latest, Week 9120, Derwent Publications Ltd., London, GB; AN 91-144175 [20] & JP-A-3 080 073 (Kyowa Hakko Kogyo KK) 4 Apr. 1991.
Chemical Abstracts Database, Columbus, Ohio, US Abstract No. 95(21):183746B, Carlson, Marian; Osmond, Barbara C.; Botstein, D. "Mutants of yeast defective in sucrose . . . " & Genetics, 98(1), 1981, 25–40.
Biosis Previews Database, Philadelphia, Abstract No. 90:48239, Caru M; Cifuentes B; Pincheira G; Jimenez A.. "Molecular Cloning and Expression in . . . " & J Appl. Bacteriol 67 (4), 1989, 401–410.

*Primary Examiner*—Mindy Fleisher
*Assistant Examiner*—Robert Schwartzman
*Attorney, Agent, or Firm*—Cushman Darby & Cushman IP Group of Pillsbury Madison & Sutro LLP

[57] ABSTRACT

New broad spectrum strains of bread-making yeast having
 a high multiplication yield,
 good nitrogen assimilation,
 preferably good resistance to drying,
characterized by the fact that they simultaneously have all the following enzymatic activities:
 maltose-permease activity after growth of the yeast on glucose medium in the absence of maltose (Test $T_1$): at least 9 units;
 maltase activity after growth of the yeast on glucose medium in the absence of maltose (Test $T_2$): at least 80 units; and
 invertase activity (Test $T_3$): less than 10 units and preferably more than 2 units.

58 Claims, 2 Drawing Sheets

1  NCYC 995
2  NCYC 996
3  Lα3
4  H037
5  HCT14
6  HCT44
7  3603
8  3608
9  3493
10 YPH80

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: NO ( x ) PUBLICATION INFORMATION:
        ( A ) AUTHORS: Taussig, Ronald
                    Carlson, Marian
        ( B ) TITLE: Nucleotide Sequence of the Yeast SUC2 Gene
              for Invertase
        ( C ) JOURNAL: Nucleic Acids Res.
        ( D ) VOLUME: 11
        ( E ) ISSUE: 6
        ( F ) PAGES: 1943-1954
        ( G ) DATE: 03-JAN-1983
        ( K ) RELEVANT RESIDUES IN SEQ ID NO:1: FROM -3 TO 21

( x i ) SEQUENCE DESCRIPTION: SEQ ID NO:1:

```
TTAGATCTAT  GATGCTTTTG  CAAGCTTTCC  TT                              32
```

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: NO ( i v ) ANTI-SENSE: YES ( x ) PUBLICATION INFORMATION:
        ( A ) AUTHORS: Taussig, Ronald
                    Carlson, Marian
        ( B ) TITLE: Nucleotide Sequence of the Yeast SUC2 Gene
              for Invertase
        ( C ) JOURNAL: Nucleic Acids Res.
        ( D ) VOLUME: 11
        ( E ) ISSUE: 6
        ( F ) PAGES: 1943-1954
        ( G ) DATE: 03-JAN-1983
        ( K ) RELEVANT RESIDUES IN SEQ ID NO:2: FROM 1588 TO 1612

( x i ) SEQUENCE DESCRIPTION: SEQ ID NO:2:

```
TTAGATCTTT  TATAACCTCT  ATTTACTTC  CCT                              33
```

STRAINS OF BREAD-MAKING YEAST, A PROCESS FOR OBTAINING SAME, AND THE CORRESPONDING FRESH AND DRY NEW YEAST

This is a continuation of application Ser. No. 08/080,131, filed on Jun. 23, 1993, which was abandoned upon the filing hereof which was a continuation of application Ser. No. 07/872,395, filed Apr. 23, 1992, abandoned.

The invention relates to new, wide spectrum strains of bread-making yeast (baker's yeast), that is to say yeasts acting both on sugar-free dough and on highly sugared doughs, and to a process for obtaining these new strains; it also relates, by way of novel industrial products, to fresh or dry bread-making yeasts obtained from these strains.

Strains which are suitable for the fermentation of maltose and relatively osmotolerant, that is to say with a wide range of application, are already known.

Reference may be had in this context to French Patent No. 7739149, European Patent No. 79 400555.3 filed on Mar. 08, 1979 and granted under the No. 0 008 554 and U.S. Pat. No. 4,396,632 of Feb. 08, 1983, all in the name of the Applicant Company.

These three Patents relate to different aspects of the exploitation of a reproducible process for obtaining new, wide spectrum strains by hybridization, which process is based on the Judicial choice of parent strains and the employment of tests for the selection of the new wide spectrum strains thus constructed.

It has also been proposed to prepare wide spectrum strains by transforming a starting strain by the integration of genes which code for enzymes providing for the fermentation of maltose (European Patent Application No. 88 201870.8 of Jan. 09, 1988 published under the No. 0 306 107). From a reading of the description it appears that the industrial results obtained are relatively poor. Thus according to Table 6, page 20 the gain obtained in ordinary dough by integrating into an osmotolerant strain an integrating vector devoid of heterologous DNA coding and containing MAD genes is 18%, which is much too little to enable the strain obtained to quality as a broad spectrum strain. In fact, the difference in activity on an ordinary dough (dough without sugar) between an osmotolerant strain which is highly active on sugared dough and a strain which is very well adapted to the fermentation of maltose may attain ratios of the order of 1 to 2. Now it would appear from a reading of the Patent that this is the only construction which may be considered as stable and liable to lead to bread-making yeasts which could be commercialized. It is also indicated on the same page 20 that the other constructions described, which apparently cannot lead to bread-making yeasts suitable for commercialization but which have led to theoretical gains of the order of 30%, which is still insufficient, would justify the idea that progress of the same order could be obtained by increasing the number of copies of integrated genes without heterologous DNA coding; this is, however, a hypothesis which remains to be verified. Now, strains of fast acting yeasts adapted to maltose, which have been used industrially for some twenty years, are strains in which, as their name indicates, the fermentation of maltose is hardly repressed at all by the presence of glucose and is not dependent to any significant extent on induction by maltose. These strains have been constructed by hybridization. When hybridization results solely from random crossing, it is a method whose results are often considered to be unpredictable and unreproducible. This is no longer true when crossing is not carried out at random and efficient selection tests are available.

Experience has shown that strains which are very well adapted to maltose are obtained with a certain frequency. Advance in the knowledge of molecular biology concerning the regulation of genes of a given system enables one to explain how, by meiotic recombination, strains having the desired properties can be constructed with a certain frequency. For example, work carried out in molecular biology has shown that mutations taking place in control genes of the system maltose MAL 13, MAL 23, MAL 43 and MAL 64 lead to strains having a constitutive expression of enzymes Which degrade maltose. These mutated genes are known as MAIL 13c, MAL 23c, MAL 43c and MAL 64c. These control genes generally have a character known as "trans" which imparts a dominant character to the mutation and their presence is often associated with a certain reduction in the repression produced by glucose. If an event can be produced with a certain frequency, the phenomenon becomes predictable and reproducible.

DETAILED DESCRIPTION OF THE INVENTION

Figure 1:
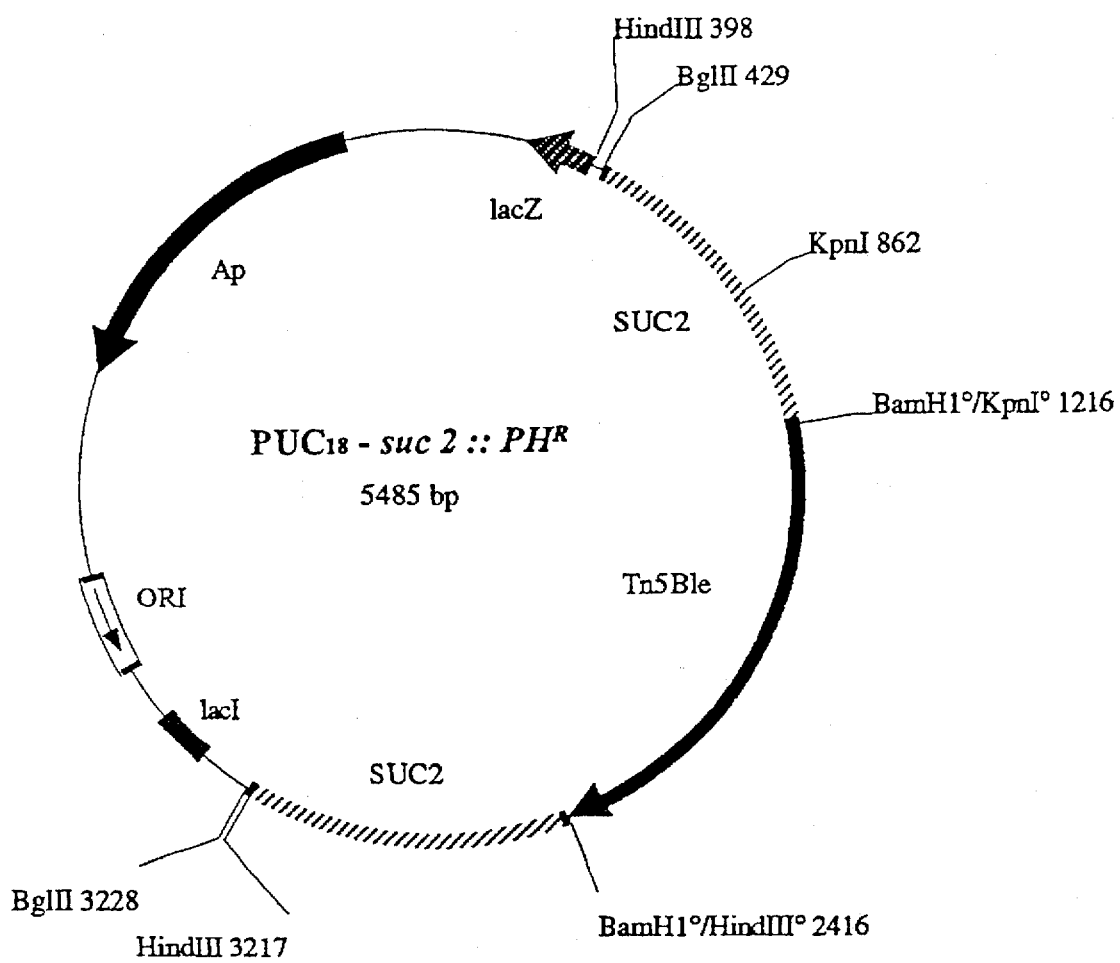
FIG. 1 shows the construction of suc 2::$PH^R$ disruption victor.

The invention in particular aims to provide new broad spectrum strains and to a reproducible process for constructing the same especially by hybridization, the said new strains and the said process constituting a significant advance compared with those of the prior art.

It is to the credit of the Applicant Company to have found, as the outcome of extensive research, that this object can be achieved, in other words that new strains of bread-making yeast which have a broad spectrum and are characterised by the following enzymatic activities determined by tests T1, $T_2$ and $T_3$ described hereinafter:

maltose permease activity after growth of the yeast on a glucose medium in the absence of maltose (Test $T_1$): at least 9 units, maltase activity after growth of the yeast on a glucose medium in the absence of maltose (Test $T_2$): at least 80 units and preferably at least 90 units, invertase activity (Test $T_3$): less than 10 units and preferably more than 2 units can be produced by carrying out a process consisting of:

selecting parent strains having in a general manner good properties of multiplication on molasses, assimilation of mineral nitrogen and preferably resistance to drying; and having particularly remarkable properties on normal dough or preferably on dough containing sugar;

sporulating the strains thus selected;

ascertaining by simple selection tests among the haploids (segregants) thus obtained those which would also have a high potential for having maxim properties on the types of bakers' doughs for which the parent strain does not perform;

crossing the high potential haploids thus selected with one another;

selecting the hybrids issuing from these crossings by the same tests and subsequently by more complete selection tests.

In complement to this process, if the invertase activity of certain obtained haploids (segregates) or certain obtained hybrids is too high, there is the possibility to lower their invertase level by genetic engineering, in particular by disrupting the gene(s) coding for the expression of invertase.

The decrease of the invertase content of bakers strain yeasts (diploids or aneuploids) or of haploids (segregates) by molecular biology, notably by disrupting one or several genes coding for invertase (SUC genes) is a technic of general scope allowing the obtention of new strains according to the invention.

The tests used to measure the aforesaid enzymatic units and the definitions of these units are indicated below.

The maltose-permease unit is expressed in nanomols of maltose entering 1 mg of yeast cell solids content per minute.

Quantitative determination of the maltose-permease after culture on a glucose medium in the absence of maltose (Test $T_1$) is based on the protocol of R. Serrano, Eur. J. Biochem., 1977, 80, 97–102, and is carried out as indicated below.

The yeasts are cultivated for 24 hours on a YES medium (yeast extract 0.5%, glucose 2%, agar 3%). The yeasts are then collected and washed to produce a suspension of yeasts containing 4 to 5 mg of dry yeast substance per ml of sodium phosphate buffer 0.05M (50 millimol), pH 6. This suspension is incubated on a water bath at 20° C. A solution containing, on the one hand, non-radioactive maltose and radioactive maltose U—$C^{14}$ for a final concentration of 1M (molar) and 22 microcuries/ml (814 kiloBecguerels/ml) and, on the other hand, 0.01M glucose (10 millimol) is prepared. The test for incorporation (entry of maltose into the cell), which is carried out at 20° C. to keep the maltose metabolism at a low level, consists of mixing 230 microliters of the yeast suspension with 30 microliters of the mixture of sugars. The speed of incorporation is estimated from the intracellular radioactivity for periods of less than or equal to 30 seconds. The malto-permease activity is expressed in nanomols of maltose entering the cell per minute and per mg of dry substance.

Quantitative determination of the maltose-permease after culture on a maltose medium (Test $T'_1$) is carried out, as indicated above, only after the yeasts have been cultivated for 24 hours on a YEM medium in which the 2% of glucose are replaced by 4% of maltose.

The maltase unit is expressed in nanomols of PNP (paranitrophenol) liberated per minute and per mg of yeast solids content.

Quantitative determination of the maltase after culture on a glucose medium in the absence of maltose (Test $T_2$) is carried out as indicated hereinafter.

The yeasts are cultivated on a YEG medium for 24 hours as for the determination of maltose-permease. The yeasts are collected and washed for preparing a suspension containing 10 to 20 milligrams of dry yeast substance per milliliter, and the yeasts are made permeable by means of chloroform by adding 0.3 ml of chloroform to 2 ml of suspension. The whole mixture is stirred for 30 minutes at 30° C. and then diluted to 20 ml with water at 4° C. The maltase is then determined by the method of H. Malvorson and E. L. Elias, Biochim. Biophys. Acta, 1958, 30, 28.

Quantitative determination of the maltase after culture on a maltose medium (Test $T'_2$) is carried out as indicated above only after the yeasts have been cultivated for 24 hours on a YEM medium in which the 2% of glucose are replaced by 4% of maltose.

The invertase unit is defined as the production of one micromol of reducing sugars, corresponding in the present case to a demi-micromol of invert sugar, in 5 minutes per mg of yeast solids content at 30° C. and pH 4.7 without plasmolysis of the yeast. For carrying out this determination (Test $T_3$), a known quantity, of the order few tenths of mg, of yeast solids content and of sucrose at a 0.1 molar concentration is introduced into a test tube containing a buffer medium (acetate buffer at pH 4.7) and placed in a water bath at 30° C. At the end of minutes, the reaction of inversion of the sugar is stopped by addition of the reagent with sodium dinitrosalicylate by means of which the quantity of reducing sugars formed is determined by a colorimetric reaction.

The values indicated above of the aforesaid characteristic enzymatic activities of the strains according to the invention show that the strains in question:

are perfectly adapted to maltose, that is to say they have maltose-permease and maltase constitutive activities in a glucose medium which are not limiting, have an invertase activity which is sufficiently powerful not to be limiting and sufficiently weak so as not to cause a rapid increase in the osmotic pressure due to hydrolysis of the sucrose.

In the case of the new strains according to the invention, the above-mentioned enzymatic activities are necessary but not sufficient conditions on their own.

The strains in question must also have a good production yield, good nitrogen assimilation, good fermentation activity on glucose since maltose or sucrose are always fermented in the form of glucose or fructose, and good resistance to drying, properties which are obtained by selection of the parent strains in accordance with the invention.

The new industrial product consisting of the breadmaking yeast prepared in the fresh form from the above-mentioned new strains obtainable by the process according to the invention is characterised by the fact that in the tests A described below, it has all the following characteristics:

in Test $A_1$ it releases from 170 to 230 ml of gas in 2 hours, in Test $A_5$ it releases from 130 to 180 ml of gas over 2 hours, preferably from 140 ml to 180 ml of gas, in Test $A_6$ it releases from 170 to 230 ml of gas over 2 hours, preferably from 180 ml to 250 ml of gas.

The new industrial product consisting of the dry breadmaking yeast prepared from the above-mentioned new strains which are obtainable by the process according to the invention is characterised by the fact that it has all the following characteristics in the tests A' described below:

in test $A'_1$ it releases from 120 to 145 ml of gas over 2 hours, in test $A'_5$ it releases from 95 to 130 ml of gas over 2 hours, preferably from 100 to 130 ml of gas, in test $A'_6$ it releases from 130 to 190 ml of gas over 2 hours, preferably from 140 to 190 ml of gas and more preferably from 150 to 190 ml of gas.

These characteristic values both of the fresh, compressed yeast according to the invention and the active dry yeast according to the invention show that the yeast is as rapid in its action on sugar-free or low sugar bakers' dough as the 'best yeasts produced for leavening sugar-free or low sugar doughs and is at least as active in its performance on dough containing more than 15% of sugar as yeasts which are specialized for the leavening of these sugar-containing doughs whereas these properties are never found side-by-side in the strains known at present.

Tests A and A' used by the Applicant for characterising the said yeasts are carried out using the fermentation meter of Burrows and Harrison described in the "Journal of the Institute of Brewing", vol. LXV, No.1, January–February 1959 and are precisely defined as follows:

Test $A_1$ (fresh compressed yeasts)

A weight of compressed yeast corresponding to a solids content of 160 mg is added to 20 g of flour incubated at 30° C., this yeast having been mixed with 15 ml of water containing 27 g of NaCl per liter and 4 g of $SO_4(NH_4)_2$ per liter. The components are mixed with the aid of a spatula for 40 seconds to form a paste which is placed on a waterbath adjusted to 30° C. 13 Minutes after the onset of mixing, the vessel containing the paste is sealed hermetically. The total quantity of gas produced is measured after 60 minutes and then after 120 minutes. This quantity is expressed in at 30° C. and under 760 mm of Hg.

For all the yeasts likely to show in 120 minutes a gas development equal to or more than 150 ml of $CO_2$, the amount of fermentescible sugars solely present in the flour is insufficient and is a limiting factor, so that the test is modified as indicated hereinafter; a weight of 106 mg of yeasts solids content is used instead of 160 mg and consequently, the reading of the quantity of gas produced is by convention multiplied by 1.5.

Test $A'_1$ (dried yeasts)

Identical to test $A_1$ but the 160 mg of yeast solids content which is in the form of dry active yeast are rehydrated for 15 minutes in distilled water at 38° C. prior to mixing. 40% of the volume of water of hydration employed is used for this purpose. The remainder of water to which 405 mg of NaCl are added is the added at the end of the 15 minutes of rehydration.

Test $A_3$ (fresh compressed yeasts)

The test is identical to test $A'_1$ but with the addition of 2 g of sucrose to the flour. The total quantity of gas produced is measured after 60 minutes.

Test $A'_3$ (dried yeasts)

Test identical to test $A'_1$ but with the addition of 2 g of sucrose to the flour. The total quantity of gas produced is measured after 60 minutes.

Test $A_4$ (fresh compressed yeasts)

Test identical to test $A_1$ but with the addition of 5.5 g of sucrose to the flour. The total quantity of gas produced is measured after 60 minutes.

Test $A'_4$ (dried yeasts)

Test identical to test $A'_1$ but with the addition of 5.5 g of sucrose to the flour. The total quantity of gas produced is measured after 60 minutes.

Test $A_5$ (fresh compressed yeasts)

Test identical to test $A_1$ but with the addition of 4 g of sucrose to the flour. The total quantity of gas produced is measured after 60 minutes and 120 minutes.

Test $A'_5$ (dried yeasts).

Test identical to test $A'_1$ but with the addition of 4 g of sucrose to the flour. The total quantity of gas produced is measured after 60 minutes and 120 minutes.

Test $A_6$ (fresh compressed yeasts)

6.5 g of icing sugar and a weight of compressed yeast corresponding to a solids content of 320 mg are added to 25 g of flour incubated at 30° C. This is followed by the same procedure as in test $A_1$ and the total quantity of gas produced is measured after 60 minutes and 120 minutes.

Test $A'_6$ (dried yeasts)

Test identical to test $A_6$; the 320 mg of yeast solids content in the form of active dry yeast is rehydrated as in test $A'_1$.

The following procedure is employed for constructing the new strains according to the invention.

The parent strains are selected in a first stage. For this selection, the best strains of bread-making yeasts already known are preferably used as these strains have indispensable basic properties. Most of these strains are obtainable from international collection centres, in particular the ATCC (American Type Culture Collection), where they are deposited.

They may be classified into two large groups, namely:

Strains which act very rapidly on sugar-free dough, which in test $A_1$ may have an activity of 200 ml of $CO_2$ or more in 2 hours as fresh yeasts but at the same the generally have activities below 70 ml of $CO_2$ over 2 hours in test $A_6$. These very rapid strains, which are very well adapted to maltose, have high constitutive maltose-permease and high constitutive maltase activities; they are also characterised by a high invertase activity;

strains which are very well adapted to sugared doughs; these may have an activity substantially exceeding 150 ml in test $A_6$ over 2 hours but their activities in test $A_1$ over 2 hours are only of the order of 100 ml of $CO_2$. These strains, which are very well adapted to sugared doughs, have weak or even very week constitutive maltose-permease activities, constitutive maltase activities and invertase activities.

Parent strains of the second group are preferably used and among these are chosen those:

which perform well in test $A_6$, that is to say which release at least 160 ml of gas in this test over 2 hours, which provide an acceptable yield on molasses, including high hourly multiplication yields, of the order of 1.20, which readily assimilate nitrogen and are capable of giving rise to breed-making yeasts under conventional culture conditions with nitrogen contents of the order of 9, based on the solids content.

These parent strains thus selected are preferably also stable against drying.

It has been found that a significant proportion of the osmotolerant strains used industrially have these properties, so that there is no difficulty in selecting suitable parent strains.

From the parent strains of the first group, those are selected:

which, on the one hand, release at least 170 ml and preferably at least 180 ml in 2 hours in test $A_1$, which give an acceptable yield on molasses, including at high hourly multiplication rates of the order of 1.20, and which readily assimilate nitrogen, and which, on the other hand, are not too osmosensitive, a feature which is ascertained by replacing the sucrose in tests $A_5$ and $A_6$ by an equal quantity of glucose, it being understood that the strains providing at least 70 ml of $CO_2$, and preferably not less than 80 ml and most preferably not less than 90 ml in 2 hours in test $A_5$, where the sucrose has been replaced by an equal quantity of glucose, are chosen (retained).

The osmosensibility of the strains can also be evaluated over 2 hours by adding to the flour of the $A_1$ test, 1 g of glucose (test Ag) in one hand, and in the other hand, 1 g of glucose+3 g of sorbitol (test $A_{10}$), and by calculating the ratio $$\frac{\text{Test } A_{10}}{\text{Test } A_9}.$$

In this test, the only strains retained must have a ratio at least equal to 0.4 and preferably at least 0.45.

In a second stage, the parent strains thus selected are sporulated.

According to the invention, among the haploids obtained, those are selected which simultaneously:

are coloured blue when cultivated on a medium based on glucose such as YEG medium (Yeast Extract 0.5%, glucose 2%, agar 3%) in the presence of 5-bromo-4-chloro-3-indolyl-alpha-D-glucopyranoside, hereinafter referred to as X alpha-glu, which is an analogue of maltose; and have an invertase level below 10 units and preferably above 2 units.

The above-mentioned blue colour test carried out in a Petri dish is very simple to perloom. The strains to be tested are picked out in checkerboard formation on a glucose based medium such as, for example, the YEG medium, containing X alpha-glu (40 microliters per Petri dish of a solution of 2% X alpha-glu in dimethylformamide). If the X alpha-glu has been able to penetrate the cell and if the maltase inside the yeast is present in a constitutive form and is not repressed by the glucose, the maltase will break the alpha-glucoside bond of this compound and release an intensely blue coloured radical which precipitates.

After growth, the colonies of the strains which have been de-repressed for the maltose system have the said intense blue colour in the test in question. This blue colour test in a Petri dish is very rapid and can be used as a simple test for rapidly testing a very large number of haploids. It is of particular interest for detecting haploids which are derepressed for the meltose system among the segregates obtained from the strains selected for their performances in test $A_6$ but which have little activity on sugar-free dough due to their lack of adaptation to maltose. It provides an astonishingly simple and reliable means of selecting, from those haploids issuing from the parent strains which are entirely unadapted to maltose, the proportion of segregates (haploids) (in the present case some percent) whose constitutive maltose-permease and constitutive maltase activities are at the necessary and sufficient levels to enable strains which are very well adapted to maltose and hence very rapid in their action on not sugared doughs to be produced by hybridisation.

Rapid measurement of the invertase level is somewhat more difficult to carry out. If, in particular, the aim is to select segregates with a low invertase level issuing from parent strains selected for their performance in test $A_1$ (release of at least 170 ml add preferably at least 180 ml over 2 hours), recourse may be had to a semiquantitative colorimetric test derived from the test carried out by TRUMBLY, Journal of Bacteriology, 1986, 166, page 1123.

A microtitration plate may be used for this purpose. 20 Microliters of water are introduced into each trough of the said plate and a quantity of the colony to be tested equal to the volume of a pinhead, that is to say about 0.05 mg of dry yeast substance (free from culture medium) is then introduced, and 50 microliters of a 6% solution of sucrose in sodium acetate buffer 0.01M (10 millimol) at pH 4.6 are then added.

The microtitration plate is then incubated for 5 minutes on a water bath at 30° C. 50 Microliters of 0.1% triphenyltetrazolium chloride in 0.5 molar NaOH are then added and incubation is again carried out on a water bath at 50° C. for 2 minutes.

A red colour develops which is all the more intense the higher the invertase level of the segregate (haploid) is. This colour test provides a sample experimental method for selecting haploids having less than 20 invertase units and preferably less than 10 invertase units.

The selection of haploids thus carried out must be confirmed by measuring their enzymatic activity.

The said haploids must have all the following activities:

maltose-permease after growth on glucose: at least 3 units and preferably at least 7 units, maltase after growth on glucose: at least 40 units and preferably at least 80 units, invertase: less that 10 units and preferably from 2 to 10 units.

These haploids will preferably also have the following activities:

maltose-permease after culture on maltose: at least 12 units.

maltase after culture on maltose: at least 200

In the next stage, hybridization of all the selected haploids is carried out, that is to say haploids which all respond to all the criteria defined above.

It should be noted that sporulation of the starting strains, obtaining the haploids and mating these haploids are carried out by the technique described in Chapter 7, "Sporulation and Hybridization of Yeast" by R. R. Fowell, in the work entitled "The Yeasts", volume 1, edited by A. H. Rose and J. S. Harrison, 1969, Academic Press. The technique of hybridization employed is the technique of mass-mating.

The strains according to the invention are then selected from all the hybrids thus obtained, using the same tests as for the selection of the haploids, namely:

development of a blue culture after they have been spread out on a Petri dish of YEG in the presence of X alpha-glu, non-development of a pink colour in the test to determine the invertase level by the method of Trumbly, maltose permease after culture of the yeast on glucose medium in the absence of maltose, at least 9 units, maltose permease after culture of the yeast on maltose medium, at least 12 units, maltase after culture of the yeast on glucose medium in the absence of maltose, at least 50 units, preferably at least 80 units and still more preferably at least 90 units, maltase after culture of the yeast on maltose medium at least 200 units, invertase: less than 10 units, preferably more than 2 units, and the selection is then narrowed down by a supplementary selection, using culture tests carried out by conventional methods:

as a function of the yield, as a function of nitrogen assimilation, as a function of the activities in tests $A_1$ and $A_6$, as a function of the resistance to drying.

To increase the possible crossbreeds and their performances, it is of interest to identify experimentally among the haploids selected as indicated above and used for cross-breeding as defined below:

those which, as a dominant character, give rise to strains having an invertase level below 10 even after they have been crossed with haploids having an invertase level above 10; and those which provide, as a dominant character, high maltose-permease and maltase activities after culture on glucose in the absence of maltose.

The experience has shown that it was less frequent to obtain the searched haploids from the strains described thereinabove as parent strains of the first group, these strains giving an important proportion of haploids with high constitutive maltose-permease and high constitutive maltase activities, but with a too high invertase level.

We have seen, however, that it was possible to lower the invertase activity of these haploids via the molecular biology, for example, by disrupting one or several genes SUC. This manipulation can also be used on the hybrids, after crossing.

To prepare the fresh bread-making yeast according to the invention, the above-mentioned strains are cultivated by the conventional methods but with a mean hourly multiplication rate of the order of 1.18 to 1.20 so as to obtain compressed yeast having a solids content of about 30% and less than 10% of budding, nitrogen contents, based on the solids content, of the order of 8.7 to 9, and $P_2O_5$ contents, based on the solids content, of the order of 3%.

The fresh compressed yeast thus obtained is characterised by the fact that:

in test $A^1$, it provides a release of gas of from 170 to 230 ml, preferably from 190 to 230 ml, over 2 hours, in test $A_5$ it provides a release of gas of from 130 to 170 ml, preferably from 140 to 180 ml, and more preferably from 150 to 180 ml over 2 hours, and in test $A_6$ it provides a release of gas of from 170 to 230 ml, preferably from 180 to 250 ml, and more preferably from 200 to 250 ml, over 2 hours.

To prepare the active dry yeast according to the invention, the new strains obtained are cultivated by the conventional methods in a concentrated medium, that is to say a medium whose total weight of wort at the end of culture in relation to the quantity of added molasses is of the order of 4.7 to 5.5 with a mean hourly multiplication rate of the order of 1.17 to 1.18 so that new compressed yeasts having a solids content of 30 to 35% are obtained, which have:

less than 5% of yeast buds, a protein content, based on the solids content, of the order of 7.9 to 8.3, a $P_2O_5$ content, based on the solids content, of the order of 2.7 to 2.8, a trehalose content, based on the solids content, of the order of 10 to 13%, preferably of the order of 12 to 13%.

This fresh yeast is dried by a rapid drying process in the presence of an emulsifier, for example in the presence of 1.5% of sorbitan monostearate.

The new dry yeast thus obtained is characterised by the fact that:

in test $A'_1$, it provides a release of gas of from 120 to 145 ml, preferably from 130 to 145 and more preferably from 135 to 145 ml over 2 hours, in test $A'5$, it provides a release of gas of from 95 to 130 ml, preferably from 100 to 130 ml, and more preferably from 110 to 130 ml, over 2 hours, and in test $A'_6$ it provides a release of gas from 135 to 190 ml, preferably from 140 to 190 ml, and more preferably from 150 to 190 ml, over 2 hours.

The invention is now illustrated with the aid of the following Examples.

EXAMPLE 1

The strains of fresh yeasts and osmotolerant dried yeasts marketed in Europe, USA and Japan are isolated.

They are tested by a culture reproducing industrial conditions in a concentrated medium at a mean multiplication rate of the order of 1.18, resulting in compressed yeasts containing 8.8–9% by weight of nitrogen, based on the solids content, dry yeasts containing 8% by weight of nitrogen, based on the solids content.

Those strains are chosen which simultaneously provide a yield of yeast solids content on beet molasses at 50 Clerget degrees (sucrose measure by double polarisation) of at least 23% and preferably at least 25%, provide compressed yeasts releasing at least 160 ml of carbon dioxide gas in test $A_6$, provide dry yeasts releasing at least 120 ml in test $A'_6$, and have an invertase level below 10 units.

The chosen strains which are not adapted to maltose are sporulated. No known strain conforming to the criteria enumerated above enables compressed fresh yeasts to be obtained which provide significantly more that 100 ml to 110 ml of gas over 2 hours in test $A_1$. A search is made for the haploids which give rise to blue colonies in the Petri dish test with YEG medium (Yeast Extinct Glucose) and X alpha-glu.

The haploids giving the blue colours are checked to confirm that they conform simultaneously to all the following criteria:

Maltose-permease activity after culture on glucose medium, at least 3 units and preferably at least 7 units, maltose-permease activity after culture on maltose medium, at least 12 units, maltase activity after culture on glucose medium, at least 40 units and preferably at least 80 units, maltase activity after culture on maltose medium, at least 200 units, invertase activity less than 10 units.

About twenty haploids conforming simultaneously to all these criteria are thus obtained.

It is mentioned here by way of example that three haploids have been deposited on Apr. 11, 1991, in the collection Nationale de Cultures de Microorganismes (CNCM) at the Pasteur Institute in Paris, 25 rue du Docteur Roux, 75724 PARIS Cedex 15. These haploids are given the following numbers in the laboratory registers of the Applicant:

HO 37 with mating sign a deposited in the CNCM under the number I-1076

HCT 14 with mating sign alpha deposited in the CNCM under the number I-1075

HCT 44 with mating sign alpha deposited in the CNCM under the number I-1074.

These haploids have the following enzymatic activities:

| | after culture on the medium | | | | |
|---|---|---|---|---|---|
| | maltose-permease glucose | maltose-permease maltose | maltase glucose | maltase maltose | invertase |
| HO 37 | 3.5 | 26 | 115 | 230 | 7 |
| HCT 14 | 8.0 | 22 | 45 | 240 | 6 |
| HCT 44 | 12.0 | 15 | 135 | 340 | 2 |

EXAMPLE 2

The haploids selected according to Example 1 are crossed with one another. The strains conforming to the following criteria are selected.

First, the strains which all have the following enzymatic activities are selected:

Maltose-permease after culture on glucose medium, at least 9 units, maltose-permease after culture on maltose medium, at least 12 units, maltase after culture on glucose medium, at least 90 units, maltase after culture on maltose medium, at least 200 units and preferably at least 230 units, invertase: less than 10 unite and preferably more than 2 units.

The performances of the strains thus selected are then verified by culture tests. Semi-anaerobic laboratory tests providing a sufficient yield for measuring the fermentative activity may be carried out. Alternatively, aerobic cultures may be made with reduced volumes. These tests have the advantage that they can be carried out rapidly on a large number of strains. They enable the strains obtained to be classified and tested to verify that they have the desired performances compared with control strains.

Lastly, tests are carried out to verify that the strains which have passed the second selection test give rise to a new breadmaking yeast according to the invention in pilot tests which reproduce as exactly as possible the conditions of industrial production, that is to say:

successive cycles of culture, concentration of the culture medium illustrated, for example by the ratio of $$\frac{\text{final weight of yeasted wort in the fermentation vat}}{\text{total molasses at 50\% sucrose}}$$

which is chosen for the test as being order of 5, and the conditions of aeration and alcohol level in the vat.

In this example, three strains were selected as providing particularly interesting new products, that is to say the new fresh compressed yeast and the new dry yeast according to the invention. These three strains are only examples and other equivalent strains may and have been obtained.

The three strains are named in the laboratory registers of the Applicant and deposited on Apr. 11, 1991, in the Collection Nationals de Cultures de Microorganismes, 25 rue du Docteur Roux, 75724 PARIS Cedex 15 under the numbers:

No. 3493 deposited in the CNCM under the No. I-1073

No. 3603 deposited in the CNCM under the No. I-1072

No. 3608 deposited in the CNCM under the No. I-1071.

These three strains have the following enzymatic activities, which are compared with the enzymatic activities of several types of strains.

| | after culture in a medium of | | | | |
|---|---|---|---|---|---|
| | Maltose-permease glucose | Maltose permease maltose | Maltase glucose | Maltase maltose | Invertase |
| 3493 | 14 | 21 | 130 | 240 | 5 |
| 3603 | 16 | 27 | 230 | 330 | 4 |
| 3608 | 16 | 36 | 90 | 250 | 8 |
| Strain isolated from a yeast acting very rapidly on ordinary dough marketed in Great Britain | 9 | 12 | 90 | 230 | 100 |
| Strain isolated from a very osmo tolerant yeast marketed in Japan | 1 | 14 | 20 | 130 | 1.5 |
| NCYC 995 | 8 | 16 | 110 | 290 | 40 |
| NCYC 996 | | 24 | | | 20 |

Figure 2:
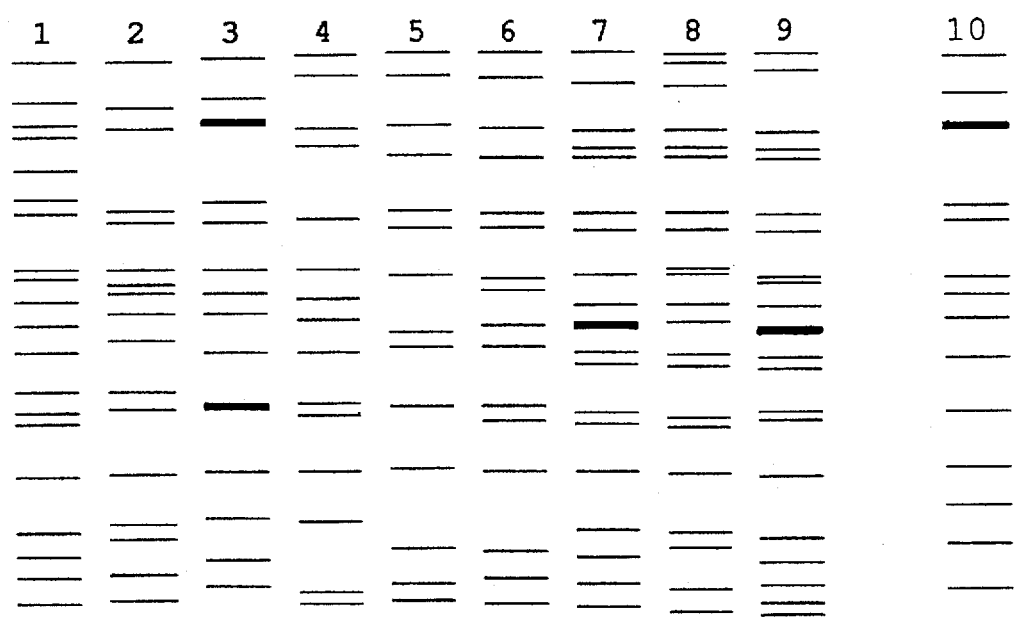
FIG. 2 shows the karyotypes according to pulsed field electrophoresis of the three haploids, HO 37, HCT 14, and HCT 44, and the three strains, 3493, 3603 and 3608.

The three haploids, HO 37, HCT 14, and-HCT 44, and the three strains, 3493, 3603 and 3608 have the karyotypes according to pulsed field electrophoresis, as shown in FIG. 2.

The strains of baker's yeast NCYC 995 and NCYC 996, which are an object of U.S. Pat. No. 4.396.632, and the following two laboratory control strains were added to this scheme as controls;

Lα3: Laboratory control haploid strain

YPE80: Yeast chromosome PPG Marker, sold by New England BIOLABS, 32 Tozer Road, Beverly, Mass. 01915/USA.

EXAMPLE 3

The three new strains, 3493, 3603 and 3608 deposited in CNCM under the numbers I-1073, I-1072 and I-1071, the strain isolated from the fresh yeast which is the best for its performances on ordinary dough, marketed in Great Britain in 1990 and referred to hereinafter as rapid British strain, and the strain isolated from the yeast which is the best for its performances on highly sugared doughs, found on the Japanese market in 1990 and referred to hereinafter as Japanese osmotolerant strain, were cultivated as follows.

With the exception of the use of processes and materials specified hereinafter, the strains were propagated in several stages of aerobic multiplication and the fresh yeast was collected, washed and filtered, using the conventional materials employed in yeast production and the conventional manufacturing processes, such as the materials and processes described in "Yeast Technology" by Gerald Reed and Henry J. Peppler (1973), the Avi Publishing Company Inc. or in the chapter "Production of Baker's Yeast", Gerald Reed, published by Prescott and Dunn's Industrial Microbiology, 4th Edition, edited by Gerald Reed, The Avi Publishing Co. Inc., second printing 1983.

Particular care was taken to ensure that all the nutriments required in small quantities in yeast, minerals (macroelements and oligoelements) and vitamins (biotin and group B vitamins) were present at least in the largest quantities recommended in the reference works cited above. These tests are in general carried out as indicated in the preceding Patents of the Applicant mentioned above. Particular care was taken to obtain the yeasts in a well washed condition and to chill the cream and the filtered yeasts rapidly to 2° C.

The last stage of multiplication of the yeast resulting in a highly active compressed fresh yeast is more specifically carried out as follows:

dilution of the culture medium at the end of commercial multiplication:

$$\frac{\text{Weight of yeasted wort in the vat}}{\text{Quantity of molasses with 50\% total sugar content expressed as sucrose}} = 5.2$$

These tests are preferably carried out with a mixture of 90% of beet molasses and 10% of cane molasse, these molasses (beet molasse and blackstrap molasse) should be of good quality, i.e. having high purity and not containing inhibitors or toxic substances for yeasts. It shall be particularly checked by tests on control cultivations that molasses do not contain toxic additives sometimes added during the extraction and purification work of sugar in sugar factory. The sugar of the beet molasses is measured by Clerget's method (determination of sucrose by double polarization), the sugar of the cane molasses is determined by enzymatic measurement of the sucrose, glucose and fructose actually present, and the totality of these sugars is calculated in sucrose equivalents;

mean hourly rate of multiplication in the lust multiplication cycle of 14 hours: 1.18 to 1.20.

maximum proportion of yeast buds collected: 10%.

proportion of nitrogen/yeast solids content collection: 9% (8.6 to 9.2).

proportion of $P_2O_5$/yeast solids content collected:

proportion of $P_2O_5$/yeast solids content collected: 3%.

These tests gave fresh bread-making yeast of about 30% of dry matter with the characteristics hereinafter given:

|  | Test A1 2 hours | Test A5 2 hours | Test A6 2 hours |
| --- | --- | --- | --- |
| Strain 3493 | 198 | 154 | 215 |
| Strain 3603 | 193 | 150 | 223 |
| Strain 3608 | 210 | 165 | 235 |
| Strain NCYC 995 | 180 | 110 | 135 |
| British rapid strain | 210 | 90 | 55 |
| Japanese osmotolerant strain | 110 | 135 | 198 |

Strain NCYC 995 was the best strain hitherto known for combining the properties of speed on normal dough (without sugar) and on sugared doughs. In the above Table, it has a nitrogen content of 8.6, based on the solids content, which is close to the maximum for industrial production of that strain.

EXAMPLE 4

The procedure is the same as in the preceding Example, using the same strain with the object of obtaining active dry yeasts. The general culture conditions remain substantially the same. The mean hourly multiplication rate is of the order of 1.18. The particular culture conditions, in particular the flow of molasses and ingredients, are adapted to provide the following composition for the collected yeast which is to be dried:

Nitrogen based on solids content optimum value (8%)

$P_2O_5$ based on solids content 2.7 to 2.8%

Trehalose based on solids content 12%

Maximum proportion of yeast buds for the obtained commercial yeast: 5%.

For the production of fresh and dried yeasts there exists for each strain an optimum nitrogen content, based on the solids content, depending on the other desired properties of the yeast. Upwards of a certain protein content, the gains in fermentative activity become low, indeed very low or even zero. This concept is very important for dry yeasts. Upwards of a certain protein content, the gains in fermentative activity do not compensate the increase in losses by drying associated with this protein content. For new strains, the optimum composition in terms of nitrogen content based on solids content is of the order of 8 to 8.3% for the production of dry yeasts.

To this yeast is added a fine emulsion based on an emulsifier such as sorbitan monostearate added in a proportion of 1.5% of the yeast solids content. The emulsion may also contain a thickener. The composition obtained is extruded through a screen having a mesh width of 0.5 to 1 mm and the said yeast is dried to a solids content of at least 92%, preferably at least 94%, by a careful rapid drying process, that is to say drying within less than one hour with the temperature of the yeast not exceeding 30° C. at the onset of drying and 40° C. at the end of drying. A fine emulsion of sorbitan monostearate is preferably added in a proportion of 15%, based on the yeast solids content, and carboxymethyl cellulose in a proportion of 0.5%, based on the yeast solids content, and the yeast is rapidly dried by fluidization in a current of hot, dry air as indicated on page 6 of European Patent 0 008 554. The dry yeast at the outlet of the fluidizer is rapidly chilled and packaged in hermetically sealed packages under an inert atmosphere, that is to say under a neutral gas (nitrogen, carbon dioxide) containing less than 1% of oxygen. Dry yeasts having a solids content of about 95% are thus obtained.

| Strain | N/solids content | Fresh yeasts with 30–35% solids content | | | Dry yeasts with 95% solids content | | |
| --- | --- | --- | --- | --- | --- | --- | --- |
| | | $A_1$ 2 hrs | $A_5$ 2 hrs | $A_6$ 2 hrs | $A'_1$ 2 hrs | $A'_5$ 2 hrs | $A'_6$ 2 hrs |
| Strain 3493 | 8–8.2 | 172 | 140 | 200 | 137 | 113 | 160 |
| Strain 3603 | 8 | 182 | 147 | 220 | 122 | 105 | 150 |
| Strain 3608 | 8 | 193 | 151 | 226 | 135 | 115 | 170 |
| Strain NCYC 995 | 7.5–7.8 | 154 | 100 | 125 | 131 | 82 | 100 |
| Strain NCYC 996 | 7.2–7.5 | 105 | 125 | 165 | 91 | 100 | 130 |
| British rapid strain | 8.2 | 185 | 90 | 70 | 125 | 60 | 40 |
| Japanese osmo-tolerant strain | 8 | 95 | 120 | 180 | 70 | 95 | 145 |

Example 5

Disruption of a gene coding for invertase in haploid strains (segregates) or hybrids (diploids or aneuploids) having high constitutive maltose permease activities and high constitutive maltase activities but also high invertase activities.

1—Technique of disruption of a gene coding for invertase in a strain of *Saccharomyces cerevisiae*.

11) cloning of the coding part (=coding region) of the SUC 2 gene by PCR (Polymerase chain Reaction) or genic amplification The sequence of the SUC 2 gene is described in "Nucleotide sequence of the yeast SUC 2 gene for invertase", R. Taussig and M. Carlson, Nucleic Acids Res. (1989)6, 1944–1954. It is also found in European and American data banks of nucleic acid sequences (EMBL and GENBANK).

Amplification of the coding part of the SUC 2 gene by PCR has been realised with the Gone Amp kit of Perkin Elmer company (with cloned Ampli Taq) on Thermal. Cycler DNA material (Perkin Elmer, 1 avenue Franklin, Montigny-le-Brettoneux, 78054 St. Quentin en Yvelines Cedex). Two oligonucleotides which serve to initiate polymerisation have been synthesised (SEQ ID NO: 1 and SEQ ID NO:2).

- DC1:

start

5'-ttagatctATGATGCTTTTGCAAGCTTTCCTT-3'

- DC2:

stop  stop

5'-ttagatctTTTATAACCTCTATTTTACTTCCCT-3'

DC1 is complementary to the anti-sense section (=strand) at the level of the ATG initiation codon.

DC2 is complementary to the sense section and comprises the 2 STOP codons of the terminal part of the coding region of the SUC 2 gene.

A Bgl II restriction site and two projecting nucleotides were added to enable subsequent cloning of the amplified sequences in the pUC$_{18}$ plasmid (reference Yannish-Perron et al (1985) Gene 33, 103–119).

The total starting DNA (=genomic DNA) was prepared from the haploid H037 strain deposited at the CNCM under the number I-1076 by conventional methods of isolating yeast DNA (Methods in Yeast Genetics—A laboratory Course Manual—M. D. Rose, F. Winston and P. Hieter—Cold Spring Harbor Laboratory Press, Cold Spring Harbor, N.Y. (1990). This haploid strain contains a single SUC gene; the SUC 2 gene carried led by the IX chromosome. The concentration of DNA in the working solution is 300 µg/ml.

Amplification was realised on 1 µg of DKA in the presence of two DC1 and DC2 primers (final concentration for each =1 µM) and 2.5 units of Ampli Tag. The following amplification programme was employed:

1. Denaturation 7 min at 95° C.
   Pause = addition of Ampli Taq enzyme (2.5 U)
2. 1 min at 95° C. (denatureation
   2 min at 55° C. (hybridisation of primers)   } 35 cycles
   5 min at 72° C. (polymerisation)
3. 7 min at 72° C.

12) poet-PCR modification=for obtaining highly effective cloning of the PCR product Elimination of sub-products of the PCR reaction (nucleotides, enzymes, salts, oligonucleotides) by the Gene Clean kit (BIO 101 distributed by OZYME).

Filling of ends by Klenow Polymerase and phosphorylation of the ends by T4 Polynucleotide kinase.

Fresh purification of the DNA by the Gene Clean kit.

Ligation of the product of PCR (Rendered with blunt ends and phosphorylated) on itself by the T4 DNA ligase.

Digestion of the product of ligation by Bgl II (sites included in the oligonucleotides).

Ligation of the SUC 2/Bgl II gene in the open pUC$_{18}$ plasmid at the level of its only Bam E$_1$ site (reference: C. Yanish-Porron, J. Vleira and J. Messing (1985) Gene 33, 103–119).

The enzymes of restriction and modification are supplied by Boehringer-Mannheim GmbH (Postfach 310120, D-6800 Mannheim 31, Germany) and by New England Biolabs distributed in France by OZYME (Avenue Franklin, 78180 Montigny-le-Bretonneux).

The techniques employed are described in: T. Maniatis, E. F. Fritsch and J. Sambrook (1982) Cold Spring Harbor Laboratory, Cold Spring Harbor, N.Y.

13) Disruption of the SUC2 gene by the pTEF$_1$/Tn5 Ble/tcyc$_1$ (PH$^R$) gene conferring resistance to phleomycin Introduction of the Tn5 Ble gene or resistance to phleomycin under yeast promoter and terminator (pTEF$_1$ and tcyc$_1$) at the level of the single Barn E$_1$ site of SUC 2.

Isolation of the pTEF$_1$/Tn5Ble/tcyc$_1$ gene of the pUT332 plasmid by Kpnl and Hind III digestion. Origin of the plasmid: supplied by CAYLA, retailer of phlemomycine (Centre Commercial de Gros, Avenue de Larrieu, 31094 TOULOUSE).

Reference: A. Gatignol, M. Dassain and G. Tiraby—Cloning of Saccharomyces cerevisiae promoters using a probe vector based on phleomycin resistance—Gene (1990) 91, 35–41.

Filling of ends of the pTEF$_1$/Tn5Ble/tcyc$_1$ gene (to obtain blunt ends) by Klenow Polymerase.

Opening of the pUC$_{18}$-SUC2 plasmid (described at 12) by Bam H$_1$ (only site situated at the middle of SUC 2). Filling of the Dam H1 ends by Klenow Polymerase and dephosphorylation by CIP (Calf Intestine Phosphatase)

→obtaining of dephosphorylated blunt ends.

Cloning of the pTEF$_1$/Tn5Ble/tcyc$_1$ gene blunt ends in the plasmid pUC$_{18}$-SUC 2 at the level of its filled and dephosphorylated Bam H1 site.

→obtaining of the pUC$_{18}$-suc 2::PH$^R$ plasmid described in FIG. 1.

14) preparation of the transforming DNA

Digestion of the pUC$_{18}$-suc 2::PH$^R$ plasmid by Kpnl and Hind III. (PH$^R$ means: resistant to phleomycin)

Isolation of the Kpn I/Hind III fragment of 2 355 pb by the Gene clean kit (BIO 101, distributed by OZYME).

15) disruption of an suc gene in a haploid, dipoid or aneuploid strain of yeast

For example, the disruption may be carried out as follows:

Transformation of the gene by electroporation (JOUAN electropulsator) by the technique described in Biotechnology (1990) 8, 223–227—E. Mealhoc, J. M. Masson and J. Tessie—High efficiency transformation of intact yeast cells by electric field pulses.

Parameters of transformation: 10$^8$ cells/50 µl—one pulse of 15 msec—2500 v/cm-Quantity of transforming DNA: 1 µg.

Selection of transforming clones for the resistance to phleomycin in a Petri dish containing a YEG agar medium supplemented by the addition of 100 µg/ml of phleomycin (CAYLA) and a low invertase level (see colorimetric test with triphenyl tetrazolium chloride described earlier on in the present specification).

It must be understood that other methods of transformation may also be used, such as the lithium chloride technique, and markers other than phleomycin may be used.

16 Construction of a perfectly homologous yeast strain containing only yeast DNA 161. Creation of a deleted suc 2Δ gene The procedure may, for example, be carried out as follows: The plasmid pUC$_{18}$-SUC 2 described at 12 is open at the level of the single Bam H1 site situated in the middle of the coding part of SUC 2 (nucleotide 787 position, counting the A of ATG as nucleotide No. 1).

The generated Bam H1 ends serve as starting point for the exonuclease Bal 31 which recurrently and simultaneously degrades the two sections (=strands) of the DNA duplex in the two senses, thus creating a deletion in SUC 2. Hydrolysis by Bal 31 is carried out under the conditions described by Maniatis et el. The reaction is stopped when about 150 nucleotides have been eliminated on either side of the BamH$_1$ site.

The DNA is then repaired by the Klenow polymerase to produce blunt ends and brought into ligation to give rise to the plasmide pUC$_{18\ -suc}$ 2Δ plasmid. This plasmid is amplified by transforming the strain of *E. coli* DH5α (marketed by GIBCO-BRL, 14 rue des Oziers, BP 7050,95051 Cergy-Pontoise Cedex). The deletion is controlled by cartography of restriction of the pUC$_{18}$-suc 2Δ plasmid obtained.

It must be understood that the non-expression of an SUC gene may equally well be obtained by other technical means, such as the introduction of a point mutation, for example by PCR, leading to the introduction of stop codons at the beginning of the coding part of the SUC gene, which gives rise to premature arrest of the translation. One may equally intervene by mutation directed on the promoter so that transcription of the gene will only take place to a slight extent, if at all.

162. Construction of a low invertase haploid, diploid or aneuploid strain by homologous genetic recombination, bringing into play only the DNA of yeast The construction of such a strain may be realised by a classic technique of co-transformation, for example:

The pUC$_{18}$-suc 2 plasmid is digested by kpnI and Hind III. The KpnI-Mind III fragment of suc 2 (≈900 pb) is then purified with the Gene Clean kit.

The yeast strain whose potential for invertase activity is required to be lowered is cotransformed by electroporation by the Kpn I-Hind III fragment of suc 2 described above and the pUT 332 plasmid, which are used in a molar ratio of 10:1. The pUT332 described above is a bacteria-yeast shuttle (navette) plasmid containing the gene for resistance to phleomycin. The selection of the PH$^R$ transformers (PH$^R$= resistant to phleomycin) is obtained by spreading the transformed cells out on Petri dishes of YEG agar medium supplemented with 100 μg/ml of phleomycin (CAYLA).

The PH$^R$ clones with diminished invertase activity are selected by means of the colorimetric test with triphenyl tetrazolium chloride described above.

The desired PH$^R$ clone with low invertase activity is freed from the pUT 332 plasmid by culture of a large number of generations on a liquid YPG medium (yeast extract 1%, bactopeptone 2%, glucose 2%) without phleomycin. A subclone which has become sensitive to phleomycin is then selected.

The absence of any trace of bacterial plasmid DNA or of resistance marker may be verified by a classical technique of Southern blot (Maniatis et al, 982), using plasmid pUT 332 marked, for example, with $^{32}$P. The occurrence of integration of the sac 2 gene instead of and in place of an intact SUC gene may also be controlled by the same technique, using the SUC 2 gene as probe.

The technique or co-transformation described above may also be used, for example, for replacing the suc 2:: PH$^R$ gene integrated with a yeast strain by the suc 2 gene prepared as described under 161. In that case, the Kpn I-Hind III fragment of the pUC$_{18}$-suc 2 plasmid is introduced by co-transformation in the presence of a bacterium-yeast shuttle plasmid containing a marker gene of resistance to an antibiotic other than phleomycin, lot example geneticin, cycloheximide, a herbicide . . . In that case, a search is made among the transforming clones which are resistant to the chosen antibiotic to find those which have become sensitive to phleomycin, and the shuttle plasmid which confers the second resistance is then eliminated, as described above.

Replacement of an SUC gene of a yeast strain by a mutated or deleted SUC gene may also be achieved by techniques other than the technique of co-transformation, as for example the technique of "jettisoning" described in European Patent E. P. 163491.

2—Application of the protocol described above to the 3597 strain

The strains which act very rapidly on sugar-free dough conforming to the selection criteria defined for the parent strains of the first group:

release of at least 170 ml of gas in 2 hours in test A1 good yield on molasses;

sufficiently low osmosensitivity (or good osmotolerance) evaluated by the tests described above, give rise to segregates (haploids) having the following activities:

constitutive maltose permease, that is to say maltose permease measured after growth on glucose: at least 7 units;

constitutive maltase, that is to say maltase measured after growth on glucose: at least 80 units;

invertase generally more than 20 units.

A series of haploids obtained with these characteristics, that is to say having an invertase activity above 20 units, was crossed with the HO37 haploid.

Hybrid strains were obtained which after culture as described in Examples 2 and 3 had high activities in test A1 but mediocre activities in tests A5 and A6. One Strain, the strain 3597, appeared to be particularly interesting on account of its activity in test A1 and its high yield on molasses. It was verified that this 3597 strain provided a Test A 10/Test A 9 ratio of at least 0.45 and that it was therefore of low osmosensitivity, but that it systematically gave rise to yeasts having an invertase activity of at least 50 units.

It was decided to disrupt at least one of the SUC genes of this strain. This was carried out as described above. The culture tests according to Example 3 and 4 were carried out on strain 3597 D 78/1 which always still contained the gene of resistance to phleomycin, which can be eliminated by the method described adore. The disruption of a single SUC gene on the 3 SUC genes carried by this hybrid strain had the effect of dividing its invertase activity by about 5 and increasing the activity of this strain by 20% in tests A5 and A6. The 3597 D 78/1 strain gives rise to yeasts having an invertase activity of the order of 10 units.

Strain 3597 D 78/1 cultivated according to Example 3 gives rise to a fresh yeast with a solids content of about 30% having the following characteristics:

| Nitrogen/ solids content | Test A1 | Test A5 | Test A6 |
|---|---|---|---|
| 9.12 | 195 | 149 | 192 |

This transformed 3597 D 78/1 strain was deposited 31 the CNCM under the No. I-1202 on 13th Apr. 1992. at the NCYC (National Collection of Yeast Cultures—AFRC Institute of Food Research—Norwich Laboratory—Norwich Research Park—Colney Lane—Norwich NR4 7UA—U.K.) under the No. NCYC 2383 on 15th Apr. 1992.

This example of transformation was carried out on a hybrid strain rot the purpose of demonstration and to show that this technique enables the desired result to be obtained. This technique will preferably be applied to the haploids (segregates) and preferentially to haploids containing at the most 1 or 2 suc genes. It is thus certain that haploids conforming to all the required criteria and giving rise to new strains of yeast for bread making corresponding to the invention will be obtained from the rapid strains which have a low osmosensitivity, that is to say which conform to the tests described.

EXAMPLE 6

Characterisation of the new bread making yeasts obtained. Obligation to carry out comparison test.

The bread making yeasts can only be characterised by their main function: their fermentative activity, that is to say their power to release gas in conventional tests reproducing different conditions of bread making fermentation. The significance of these tests is discussed in Example 7.

The bread making yeasts cannot be characterised in any other way, they are in fact obtained by employing at least two means:

a strain;

a process of culturing this strain;

completed by processes of harvesting, filtration, extrusion, drying and conditioning which must take account the viability of the yeast cells.

The strain is an essential means but on the one hand this is only one means; the characteristics of the process of culturing are equally important, and on the other hand the processes of constructing new strains generally lead to several equivalent strains.

The process of culturing is composed of several anaerobic phases followed by several aerobic phases of multiplication of the starting strain, as described in the reference works. The most important phase is the last cycle of multiplication leading to the pressed yeast which is to be sold commercially in the form of pressed yeast with a solids content of about 30% or dried to a solids content of at least 94%.

The characteristic parameters of this last multiplication cycle of which the duration is of the order of 14 hours, are as follows:

dilution of the culture medium at the end of the cycle (or concentration of the culture media in cells and not assimilated organic and mineral elements);

the mean hourly multiplication rate during the last multiplication cycle, it being understood that this hourly rate is higher at the beginning of the cycle and lower at the end of the cycle, the choice of the multiplication curve enabling the concentration of buds and the composition of the yeast to be regulated;

the desired composition of the yeasts at the stage of harvesting;

it being understood that with these characteristics, the man of the art having knowledge of the documents cited in the present Application and in particular the prior Patents of the Applicant as well as the reference works, in particular all the works written or published by Gerald Reed, has all the elements at his disposal for defining the entire production scheme experimentally within the scope of his normal competence and knowledge. The production of highly active fresh yeasts and of dry yeasts are subject to different production schemes since the final compositions desired for the harvested yeast differ widely. Each strain requires slight adaptations. The composition of the molasses is also an important variable; in particular, the yeast producer must verify the absence of toxic or inhibitory elements in the molasses.

These realisations of the schemes, which are within the normal competence of the man of the art, must be carried out using known test strains for comparison and measuring the maximum of the parameters.

By way of attempts to eliminate the occurrence molasses, tests for realising the last multiplication cycle were carried out on classical synthetic media.

For a multiplication cycle leading to a flow rate of 850 g of sugar in 14 hours, 4 kg of starting-medium containing the following salts and vitamins were realised:

| | | |
|---|---|---|
| Potassium sulphate | $K_2SO_4$ | 101 g |
| Clacium chloride | $CaCl_2$ | 3.4 g |
| Magnesium chloride | $MgCl_2$ | 14.5 g |
| Sodium sulphate | $Na_2SO_4$ | 23 g |
| Ammonium ferrous sulphate | $(NH_4)_2Fe(SO_4)_2 \cdot 6H_2O$ | 2590 mg |
| Potassium aluminium sulphate | $KAl(SO_4)_2 \cdot 12H_2O$ | 149 mg |
| Zinc sulphate | $ZnSO_4 \cdot 7H_2O$ | 650 mg |
| Copper sulphate | $CuSO_4 \cdot 5H_2O$ | 1.5 mg |
| Cobalt chloride | $CoCl_2 \cdot 6H_2O$ | 2.1 mg |
| Sodium borate | $Na_2B_4O_7 \cdot 10H_2O$ | 2.2 mg |
| Manganese chloride | $MnCl_2 \cdot 4H_2O$ | 0.92 mg |
| Molybdenum oxide | $MoO_3$ | 0.026 mg |
| Nicotinic acid | | 188 mg |
| Mesoinositol | | 1880 mg |
| Vitamin $B_1$ | | 86 mg |
| Vitamin $B_2$ | | 3.7 mg |
| Vitamin $B_6$ | | 24 mg |
| Biotin | | 1.0 mg |
| Para-aminobenzoic acid | | 11.4 mg |
| Calcium pantothenate | | 18.8 mg |

10 g of yeast extract in powder form of the DIFCO type for culture medium, are added to this medium.

The 850 g of sugar, nitrogen and $P_2O_5$ required for the Fed batch culture are cast according to a yeast multiplication curve corresponding to the conditions defined in Example 3 or 4, according to the case. The pH is adjusted to 4–7 with sodium hydroxide solution. The final volume in the vat at the time of harvesting is 7.5 liters, containing about 1500 g of yeast substance having a solids content of 30%.

The following results were obtained:

| | | Fresh yeasts | | | Dry yeasts | | |
|---|---|---|---|---|---|---|---|
| Strain | N/ms | A1 | A5 | A6 | A'1 | A'5 | A'6 |
| NCYC 995 | 7.6 | 156 | 100 | 125 | 124 | 70 | 90 |
| NCYC 996 | 7.2 | 105 | 117 | 153 | 90 | 95 | 126 |
| 3493 | 8.3 | 170 | 140 | 199 | 128 | 111 | 166 |
| 3493 | 8.9 | 189 | 150 | 207 | | | |

It should be noted that the same classification and the same tendencies are found under these experimental conditions.

The reproducibility of biological productions may be controlled within a given laboratory or within a given centre of production but control among different laboratories and centres of production is a delicate problem. Consequently, numerous careful tests are necessary to optimise the conditions. One or more well known control strains must always be introduced into the tests so that at least a set of data with relative values obtainable.

EXAMPLE b 7

Concerning the fermentative activity tests.

The various tests used to measure the activity of Dread yeasts,are discussed in Chapter VII 1 B entitled "Appréciation du pouvoir fermentaire", pages 449 to 464 of Guide Pratique d'Analyses dans les Industries des Céréales, joint work by B. GODON and W. LOISEL, published by Techniques et Documentation Lavoisier/ April 1984. The method of Burrows and Harrison is described there as the method of choice for yeast producers.

The following tests were used in the present Patent Application:
- tests $A_1$ and $A'_1$ which correspond to the method described in detail on pages 455 to 458 of the said work and which are a repetition, except for some variations, of the original method described by its authors in 1959. They apply to a sugar-free dough;
- tests $A_5$ and $A'_5$, $A_6$ and $A'_6$ which are tests for sugared doughs.

These last tests were preferred to tests $A_2, A'_2, A'_3, A_3, A_4$ and $A'_4$, which showed through experience to be less instructive. Some culture tests were done using again the tests $A_3$, $A'_3$, $A_4$ and $A'_4$. Their results are shown in the Table below which also shows the results obtained in these tests with strains NCYC 890, NCYC 995 and NCYC 996 for comparison.

is at least as active on normal dough and is much more active on sugared dough compared with the compressed fresh yeast obtained with strain ApGb-p2RBRR01=01.

These conclusions may be extrapolated to dry yeasts. These conclusions are normal if one takes into account that the best yeasts for highly sugared doughs have an activity on sugar-free dough which is less than half those of the best yeasts which are specialized for sugar-free dough. The maximum gain on sugar-free doughs which can be hoped for by the method of transformation used in the European Patent Application published under the No. 306 107 is a few tens of percent. On the basis of the results described, this method of transformation can only lead to yeasts which are inferior in their performances to those of the present invention.

| Strain | N/solids content | Fresh yeasts 30–35% solids content | | | | | Dry yeasts 95% solids content | | | | |
|---|---|---|---|---|---|---|---|---|---|---|---|
| | | A1 2 hrs | A3 1 hr | A4 1 hr | A5 2 hrs | A6 2 hrs | A'1 2 hrs | A'3 1 hr | A'4 1 hr | A'5 2 hrs | A'6 2 hrs |
| 3493 | 8.00 | 170 | 70 | | 140 | 198 | 137 | 57 | | 113 | 175 |
| 3493 | 8.06 | 177 | 75 | | 144 | 198 | 139 | 58 | | 115 | 157 |
| 3603 | 7.94 | 182 | 73 | 48 | 147 | 220 | 122 | 51 | 35 | 105 | 150 |
| 3608 | 8.60 | 208 | 82 | 54 | 160 | 233 | 130 | 52 | 33 | 102 | 159 |
| 3608 | 7.90 | 193 | 78 | 50 | 151 | 226 | 135 | 60 | 38 | 115 | 170 |
| NCYC 995 | 7.5 | 154 | | 32 | 100 | 125 | 131 | | 26.3 | 82 | 100 |
| NCYC 996 | 7.2 | 105 | | 41 | 125 | 165 | 91 | | 34 | 100 | 130 |
| NCYC 890 | 7.8 | 145 | 58 | 33 | | | 128 | 50 | 27.5 | | |

In European Patent Application No. 88 201 870.8 published under the No. 0 306 107, in which wide spectrum strains are obtained by different means tests named B, C and B', C', which are specific to the Applicant of this European Patent, were used. The breadmaking yeast obtained with a strain transformed by the integration of homologous vectors has never been offered for sale, according to the most recent declarations by a spokesman of the Applicant of the said Patent. No transformed strain has been deposited at a centre of collections. Tests B and C are tests used on normal, sugar-free dough and tests B' and C' are for dough containing 30% sugar. Since no samples could be obtained, a correlation test between the results obtained:
- by the said tests B and C on the one hand and tests $A_1$ and $A'_1$ on the other hand, and
- by the said tests B' and C' on the one hand and tests $A_6$ and $A'_6$ on the other hand was carried out. The following Table may be drawn up from the results of this correlation test:

| | Fresh compressed yeast having a solids content of about 30% | | | |
|---|---|---|---|---|
| | B | A1 | B' | A6 |
| Strain A of Application 306 107 | ≈311 | 155 | ≈190 | 122 |
| Strain ApGb P2RBRR01=1 | 367 | 184 | ≈190 | 122 |
| Strain 3493 | 396 | 198 | 333 | 215 |
| Strain 3608 | 420 | 210 | 364 | 235 |

It will be noted that very few absolute values are given and no drying test is described in European Patent Application No. 306 107. It nevertheless appears that the new compressed fresh yeast which is the object of the present invention

---

We claim:

1. Isolated man-made bread-making yeast strain having simultaneous enzymatic activity comprising the following:

maltose-permease activity after growth of the yeast on glucose medium in the absence of maltose (Test $T_1$) of at least 9 units;

maltase activity after growth of the yeast on glucose medium in the absence of maltose (Test $T_2$) of at least 80 units; and invertase activity (Test $T_3$) of less than 10 units.

2. Bread-making yeast strain according to claim 1 further comprising:

a high multiplication yield;

good nitrogen assimilation;

good glucose fermentation activity; and good resistance to drying.

3. Bread-making yeast strain according to claim 1, wherein the maltase activity is at least 90 units.

4. Bread-making yeast strain according to claim 1, wherein the invertase activity (Test $T_3$) is more than 2 units.

5. Bread-making yeast strain according to claim 1, having enzymatic activities further comprising:
   maltose-permease activity after growth of the yeast on maltose medium (Test $T'_1$) of at least 12 units, and
   maltase activity after growth of the yeast on maltose medium (Test $T'_2$) of at least 200 units.

6. Bread-making yeast strain according to claim 1, wherein said yeast strain is deposited in the Collection Nationale de Cultures de Microorganismes at the Pasteur Institute under the No. I-1073.

7. Bread-making yeast strain according to claim 1, wherein said yeast strain is deposited in the Collection Nationale de Cultures de Microorganismes at the Pasteur Institute under the No. I-1072.

8. Bread-making yeast strain according to claim 1, wherein said yeast strain is deposited in the Collection Nationale de Cultures de Microorganismes at the Pasteur Institute under the No. I-1071.

9. Bread-making yeast strain according to claim 1, wherein said yeast strain is deposited in the Collection Nationale de Cultures de Microorganismes at the Pasteur Institute under the No. I-1202 and at the National Collection of Yeast Cultures under the No. 2383.

10. Bread-making yeast obtained by a cultivation process of isolated man-made yeast strain according to claim 1.

11. Process for producing the bread-making yeast strain of claim 1 comprising:
   a) selecting parent bread-making yeast strains from those
      1) which belong to a first or to a second group, the first group consisting of those bread-making yeasts having good leavening on sugared dough and give rise to fresh yeasts releasing at least 160 ml of gas in 2 hours in Test $A_6$ and the second group consisting of those having good leavening on normal dough and give rise to fresh yeasts releasing at least 170 ml of gas in 2 hours in Test $A_1$ and which further have low osmosensitivity, and enable production of fresh yeasts which:
         either give rise to at least 70 m in 2 hours in Test $A_5$ in which the saccharose has been replaced by an equal quantity of glucose
         or give rise with respect to a Test Ag and a Test $A_{10}$ to a ratio of Test $A_{10}$ Test Ag at least equal to 0.40 and;
      2) which provide an acceptable yield on molasses including at high hourly multiplication rates of the order of 1.20; and
      3) which easily assimilate nitrogen and give rise to bread-making yeasts under current culture conditions with nitrogen content of the order of 8.6 to 9.2%, based on the solids content;
   b) sporulating the selected parent strains;
   c) selecting among the haploids (segregates) thus obtained by simple selection tests to estimate and then to measure their enzymatic activities, those haploids which have good bread-making properties, based on said enzymatic activities, on the type of baking doughs for which the parent strains are not active;
   d) crossing the haploids thus selected; and
   e) selecting hybrids obtained from said crossing, to be those hybrids resulting in said enzymatic activities.

12. Fresh bread-making yeast according to claim 10, having a solids content of about 30% and having further characteristics comprising:
   in a Test $A_1$, said yeast produces a release of gas of from 170 to 230 ml, over 2 hours;
   in a Test $A_5$, said yeast produces a release of gas of from 130 to 180 ml, over 2 hours; and
   in a Test $A_6$, said yeast produces a release of gas of from 170 to 250 ml, over 2 hours.

13. Dry bread-making yeast according to the bread-making yeast of claim 10 which has been subjected to a drying step in the presence of an emulsifier, said dry bread-making yeast having a solids content of at least 94% and further characteristics comprising:
   in a Test $A'_1$, said yeast produces a release of gas of from 120 to 145 ml. over 2 hours;
   in a Test $A'_5$, said yeast produces a release of gas of from 95 to 130 ml, over 2 hours; and
   in a Test $A'_6$, said yeast produces a release of gas of from 135 to 190 ml, over 2 hours.

14. A method of leavening sugar-free and sugared bakers' dough comprising the step of mixing with said dough a leavening effective amount of the bread-making yeast according to claim 10.

15. The process according to claim 11, wherein the haploid of step c) is deposited in the Collection Nationale de Cultures de Microorganismes (CNCM) at the Pasteur Institute under the No. I-1076.

16. The process according to claim 11, wherein the haploid of step c) is deposited in the Collection Nationale de Cultures de Microorganismes (CNCM) at the Pasteur Institute under the No. I-1075.

17. The process according to claim 11, wherein the haploid of step c) is deposited in the Collection Nationale de Cultures de Microorganismes (CNCM) at the Pasteur Institute under the No. I-1074.

18. The process according to claim 11, wherein said haploid (segregates) selected in step c), are subjected to disruption of at least one of the SUC genes coding for invertase in order to lower the level of invertase activity.

19. The process according to claim 11, wherein the release of gas in Test $A_1$ performed on the selected parent bread-making yeast strains is at least 180 ml.

20. The process according to claim 11, wherein the release of gas in Test $A_5$ performed on the selected parent bread-making yeast strains is at least 80 ml.

21. The process according to claim 11, wherein the release of gas in Test $A_5$ performed on the selected parent bread-making yeast strains is at least 90 ml.

22. The process according to claim 11, wherein the release of gas in Tests $A_9$ and $A_{10}$ performed on the selected parent bread-making yeast strains is such that the ratio Test $A_{10}$/Test $A_9$ is at least equal to 0.45.

23. The process according to claim 11, comprising selecting from haploids obtained by sporulation of the parent strains, those haploids which simultaneously have characteristics including:
   1) blue coloration when cultivated on a medium based on glucose in the presence of 5-bromo-4-chloro-3-indolyl-alpha-D-glucopyranoside or X alpha-glu;
   2) show lack of development of a pink color in a Trumbly test for determining invertase level;
   3) maltose-permease enzymatic activity after culture on glucose of at least 3 units;
   4) maltase enzymatic activity after culture on glucose of at least 40 units; and
   5) an invertase level below 10 units.

24. The process according to claim 11, wherein the invertase level is above 2 units.

25. The process according to claim 11, wherein the maltose-permease enzymatic activity is at least 7 units.

26. The process according to claim 11, wherein the maltase enzymatic activity is at least 80 units.

27. The process according to claim 11, wherein the step e) consists of selecting among said hybrids those having the following characteristics:
1) show development of a blue colored culture after they have been spread on a YEG Petri dish in the presence of X alpha-glu;
2) show lack of development of a pink color in a Trumbly test for determining invertase level;
3) maltose-permease enzymatic activity after culture on glucose medium in the absence of maltose of at least 9 units;
4) maltose-permease enzymatic activity after culture on maltose medium of at least 12 units;
5) maltase enzymatic activity on glucose medium in the absence of maltose of at least 50 units;
6) maltase enzymatic activity on maltose medium of at least 200 units; and
7) invertase enzymatic activity of less than 10 units, with the caveat that among the hybrids thus selected, an additional selection using culture tests is carried out for those hybrids optimizing the following industrial criteria:
yield on molasses,
assimilation of nitrogen,
activities of bread-making yeast obtained by applying Tests $A_1$ and $A_6$, and
resistance to drying.

28. The process according to claim 11, wherein at least two haploids selected from the group consisting of I-1074, I-1075 and I-1076, are crossed with one another and among hybrids obtained from these crossings, hybrids are selected having characteristics including:
1) show development of a blue colored culture after they have been spread on a YEG Petri dish in the presence of X alpha-glu;
2) show lack of development of a pink color in a Trumbly test for determining invertase level;
3) maltose-permease enzymatic activity after culture on glucose medium in the absence of maltose of at least 9 units;
4) maltose-permease enzymatic activity after culture on maltose medium of at least 12 units;
5) maltase enzymatic activity on glucose medium in the absence of maltose of at least 50 units;
6) maltase enzymatic activity on maltose medium of at least 200 units; and
7) invertase enzymatic activity of less than 10 units, with the caveat that among the hybrids thus selected, an additional selection using culture tests carried out by conventional methods is carried out for those hybrids optimizing the following industrial criteria:
yield on molasses,
assimilation of nitrogen,
activities of bread-making yeast obtained by applying Tests $A_1$ and $A_6$, and
resistance to drying.

29. The process according to claim 11, wherein: in step a), parents are selected among those which belong to the group of those having good leavening on sugared dough and give rise to fresh yeast releasing at least 160 ml of gas in 2 hours in Test $A_6$, and in step c), the selected haploids are those which simultaneously present characteristics including:

1) blue coloration when cultivated on a medium based on glucose in the presence of 5-bromo-4-choro-3-indolyl-alpha-D-glucopyranoside or X alpha-glu;
2) an invertase level below 10 units;
3) maltose-permease enzymatic activity after culture on glucose of at least 3 units; and p1 4) maltase enzymatic activity after culture on glucose of at least 40 units.

30. Bread-making yeast according to claim 12, wherein the release of a gas in Test $A_1$ is from 190 to 230 ml.

31. Bread-making yeast according to claim 12, wherein the release of a gas in Test $A_5$ is from 140 to 180 ml.

32. Bread-making yeast according to claim 12, wherein the release of a gas in Test $A_5$ is from 150 to 180 ml.

33. Bread-making yeast according to claim 12, wherein the release of a gas in Test $A_6$ is from 180 to 250 ml.

34. Bread-making yeast according to claim 12, wherein the release of a gas in Test $A_6$ is from 200 to 250 ml.

35. A method of leavening sugar-free and sugared bakers' dough comprising the step of mixing with said dough a leavening effective amount of the bread-making yeast according to claim 12.

36. Bread-making yeast according to claim 13, wherein the release of a gas in Test $A'_1$ is from 130 to 145 ml.

37. Bread-making yeast according to claim 13, wherein the release of a gas in Test $A'_1$ is from 135 to 145 ml.

38. Bread-making yeast according to claim 13, wherein the release of a gas in Test $A'_7$ is from 100 to 130 ml.

39. Bread-making yeast according to claim 13, wherein the release of a gas in Test $A'_5$ is from 110 to 130 ml.

40. Bread-making yeast according to claim 13, wherein the release of a gas in Test $A'_6$ is from 140 to 190 ml.

41. Bread-making yeast according to claim 13, wherein the release of a gas in Test $A'_6$ is from 150 to 190 ml.

42. A method of leavening sugar-free and sugared bakers' dough comprising the step of mixing with said dough a leavening effective amount of the bread-making yeast according to claim 13.

43. The process according to claim 23, wherein the invertase activity is lowered by disruption of at least one of the SUC genes of haploids which have characteristics including:
1) blue coloration in the test with coloring substance X alpha-glu and have a maltose-permease enzymatic activity after culture on glucose of at least 7 units and a maltase enzymatic activity after culture on glucose of at least 80 units; and
2) an invertase level above 10 units and which have been obtained from strains which result in fresh yeasts producing at least 170 ml in 2 hours in Test $A_1$ and have a low osmosensitivity.

44. The process according to claim 23, wherein the selected haploids have further characteristics including:
1) maltose-permease enzymatic activity after culture on maltose of at least 12 units; and
2) maltase enzymatic activity after culture on maltose of at least 200 units.

45. The process according to claim 27, wherein the maltase enzymatic activity after culture on glucose medium is at least 80 units.

46. The process according to claim 27, wherein the maltase enzymatic activity after culture on glucose medium is at least 90 units.

47. The process according to claim 27, wherein the invertase enzymatic activity is more than 2 units.

48. The process according to claim 27, wherein resulting hybrids having invertase enzymatic activity of 10 units or more, have their invertase activity lowered by disruption of at least one of the SUC genes of said hybrid.

49. The process according to claim 28, wherein the maltase enzymatic activity after culture on glucose medium is at least 80 units.

50. The process according to claim 28, wherein the maltase enzymatic activity after culture on glucose medium is at least 90 units.

51. The process according to claim 28, wherein the invertase enzymatic activity is more than 2 units.

52. Bread-making yeast obtained by a cultivation process of isolated man-made yeast strain deposited in the Collection Nationale de Cultures de Microorganismes (CNCM) at the Pasteur Institute under the No. I-1071.

53. Bread-making yeast obtained by a cultivation process of isolated man-made yeast strain deposited in the Collection Nationale de Cultures de Microorganismes (CNCM) at the Pasteur Institute under the No. I-1072.

54. Bread-making yeast obtained by a cultivation process of isolated man-made yeast strain deposited in the Collection Nationale de Cultures de Microorganismes (CNCM) at the Pasteur Institute under the No. I-1073.

55. Bread-making yeast obtained by a cultivation process of isolated man-made yeast strain deposited in the Collection Nationale de Cultures de Microorganismes (CNCM) at the Pasteur Institute under the No. I-1202 and at the National Collection of Yeast Cultures under the No. 2383.

56. A method of leavening sugar-free and sugared bakers' dough comprising the step of mixing with said dough a leavening effective amount of the bread-making yeast according to claim 52.

57. A method of leavening sugar-free and sugared bakers' dough comprising the step of mixing with said dough a leavening effective amount of the bread-making yeast according to claim 53.

58. A method of leavening sugar-free and sugared bakers' dough comprising the step of mixing with said dough a leavening effective amount of the bread-making yeast according to claim 54.

* * * * *